US010292371B2

(12) United States Patent
Cabibi et al.

(10) Patent No.: US 10,292,371 B2
(45) Date of Patent: May 21, 2019

(54) METHOD AND APPARATUS FOR EFFECTING SPERM COLLECTION AND ARTIFICIAL INSEMINATION IN SMALL BIRDS

(71) Applicants: Andrea Cabibi, Valley Center, CA (US); Phillip Cabibi, Valley Center, CA (US)

(72) Inventors: Andrea Cabibi, Valley Center, CA (US); Phillip Cabibi, Valley Center, CA (US)

(*) Notice: Subject to any disclaimer, the term of this patent is extended or adjusted under 35 U.S.C. 154(b) by 485 days.

(21) Appl. No.: 15/069,787

(22) Filed: Mar. 14, 2016

(65) Prior Publication Data

US 2017/0258051 A1    Sep. 14, 2017

(51) Int. Cl.

| | |
|---|---|
| *A61D 19/00* | (2006.01) |
| *A61D 19/02* | (2006.01) |
| *A01K 37/00* | (2006.01) |
| *A01K 45/00* | (2006.01) |
| *A01K 67/02* | (2006.01) |
| *A01N 1/02* | (2006.01) |
| *A61D 3/00* | (2006.01) |

(52) U.S. Cl.
CPC .............. *A01K 37/00* (2013.01); *A01K 45/00* (2013.01); *A01K 67/02* (2013.01); *A01N 1/0226* (2013.01); *A61D 3/00* (2013.01); *A61D 19/021* (2013.01); *A61D 19/027* (2013.01)

(58) Field of Classification Search
CPC ...... A01K 1/0613; A01K 67/02; A01K 15/00; A01K 1/031; A01K 45/00; A01K 45/007; A61D 3/00; A61D 19/027; A61D 19/00; A61D 19/024; A61D 1/005; A61D 2003/003; A61D 2003/006
USPC .......................... 119/752, 756, 757, 417, 6.8
See application file for complete search history.

(56) References Cited

U.S. PATENT DOCUMENTS

| | | | | | |
|---|---|---|---|---|---|
| 3,739,751 | A | * | 6/1973 | Mohr ........................ | A61D 3/00 119/752 |
| 4,378,798 | A | * | 4/1983 | Cassou ................ | A61D 19/027 604/217 |
| 4,432,753 | A | * | 2/1984 | Cassou ................ | A61D 19/027 600/35 |
| 4,478,261 | A | * | 10/1984 | Cassou ................... | B65B 3/003 141/173 |
| 4,502,418 | A | * | 3/1985 | Runyan .............. | A22C 21/0007 452/188 |

(Continued)

*Primary Examiner* — Yvonne R Abbott-Lewis
(74) *Attorney, Agent, or Firm* — MU P.C.

(57) ABSTRACT

A method of artificially inseminating a hen includes the steps of securing a male bird, applying a semen extender liquid to a tip of a cloacal protuberance of the male bird, squeezing the cloacal protuberance to extract semen from the male bird into the semen extender liquid to form a mixture, applying a tip of a pipette to the mixture, drawing the mixture into the pipette, securing the hen, inserting the pipette into the hen's cloaca, and squeezing a bulb of the pipette to inject the mixture from the pipette into the cloaca. A holding device for restraining a bird during sperm collection and artificial insemination procedures has a base, an arm extending upward from the base, and an open-ended receptacle connected to the upper end of the arm. The holding device is useful in mitigating injury to the bird and the handler during the procedures.

12 Claims, 3 Drawing Sheets

(56) References Cited

U.S. PATENT DOCUMENTS

| | | | | |
|---|---|---|---|---|
| 4,522,621 | A * | 6/1985 | Cassou | A61D 19/027 604/140 |
| 5,011,780 | A * | 4/1991 | Perry | A01K 45/00 119/6.8 |
| 5,320,069 | A * | 6/1994 | Anderson, Jr. | A61D 3/00 119/751 |
| 5,816,197 | A * | 10/1998 | DeStefano | A01K 1/0613 119/712 |
| 6,325,154 | B1 * | 12/2001 | Keeler | A01L 11/00 119/755 |
| 6,446,579 | B1 * | 9/2002 | Griebling | A01K 1/0613 119/751 |
| 6,477,986 | B1 * | 11/2002 | Korjenic | A01K 1/0613 119/757 |
| 6,573,097 | B2 * | 6/2003 | Cantrell | A01K 45/007 119/6.8 |
| 6,718,909 | B2 * | 4/2004 | Moran | A01K 45/00 119/419 |
| 7,426,904 | B2 * | 9/2008 | Zan | A61B 5/0408 119/421 |
| 8,082,879 | B2 * | 12/2011 | Moran | A01K 45/007 119/6.8 |
| 8,584,621 | B2 * | 11/2013 | Lee | A61D 3/00 119/751 |
| 8,590,487 | B1 * | 11/2013 | Goddard, Jr. | A01K 1/031 119/417 |
| 2012/0012070 | A1 * | 1/2012 | Gorans | A01K 1/0613 119/713 |

* cited by examiner

METHOD AND APPARATUS FOR EFFECTING SPERM COLLECTION AND ARTIFICIAL INSEMINATION IN SMALL BIRDS

CROSS-REFERENCE TO RELATED APPLICATION(S)

Not Applicable.

BACKGROUND OF THE INVENTION

1. Field of Invention

The present invention relates to the field of sperm collection and artificial insemination, and more particularly, a method of collecting sperm samples from, and artificially inseminating, small bird breeds.

2. Description of Related Art

Artificial insemination in larger bird species, such as cranes, has been used successfully by zoos and conservation breeding centers as a technique to save endangered species of birds. Due to the loss of habitat, changes in environment, etc., the process of artificial insemination is crucial to the survival of various species of birds. Allowing the reproduction process to occur naturally, i.e., through natural mating, can present a number of obstacles to a successful propagation of the particular species. For example, in order to successfully mate a male bird and a female bird, i.e., a hen, a pair bond must first be established. Otherwise, there is a lack of breeding performance. Further, prior to establishing the pair bond, the birds are apt to fight with one another, thus further hindering the breeding process. Furthermore, even if the birds do breed, there is the possibility that the eggs may not be fertilized. In addition, when a bird is required to be moved a long distance to be in physical proximity to an intended mate, the process can be expensive and both distressing and possibly life-threatening for the bird being moved. Also, some countries have restrictive export and import controls on live birds, particularly for rare breeds that are most desirable for breeding purposes, and most countries have expensive and time-consuming quarantine requirements. In many cases moving a bird to a distant location requires that it acclimatize to a new environment and food, which can be distressing and life-threatening.

Artificial insemination in larger bird species such as chickens and turkeys has been used successfully in the agricultural industry to assure a high probability of timely fertilization of hens resulting in the predictability and efficiency of chick production required for the industry.

In addition to preventing extinction, and increasing breeding predictability in an agricultural environment, artificial insemination is a viable alternative to natural breeding to propagate desirable and highly selective features of a particular bird breed. This is especially true for small bird species, such as canaries and finches that are owned and bred by individuals for whom fine distinctions in such features have great value. However, artificial insemination techniques used for larger breed birds, such as the cranes, chickens and turkeys discussed previously is achieved using a method of sperm collection that is not applicable to small bird species. Small bird species present a particularly unique set of issues with regard to artificial insemination due to their size. First of all, due to the extremely small size of semen samples from small bird species, the semen dehydrates during the collection process, thus making most, or all, of the sperm sample unusable. Additionally, the current techniques used for artificially inseminating small breed birds are harsh and inhumane. Typically, an insemination device is forcefully inserted into and removed repeatedly from the cloaca of the male bird to attempt to collect a sperm sample. The same pipette is then inserted and removed repeatedly from the female's reproductive organ in an attempt to introduce semen into the female's reproductive tract. This method of insemination is not only ineffective due to the dehydration of the sperm sample in the tube and contamination of the sperm sample with lymph fluid released as a consequence of damage to the cloacal area of the male during extraction of the sperm, but is both mentally and physically damaging to both the male and the hen.

In an effort to curtail issues and obstacles in the breeding process of small breed birds, it is essential to develop an alternative method of propagation of these species. Based on the foregoing, there is a need in the art for a method of semen collection from, and artificial insemination of, small breed birds that ensures successful insemination in an effective and humane manner.

SUMMARY OF THE INVENTION

A method of artificially inseminating a hen, includes the steps of securing a male bird; applying a semen extender liquid to a tip of a cloacal protuberance of the male bird; squeezing the cloacal protuberance to extract semen from the male bird into the semen extender liquid to form a mixture; applying a tip of a pipette to the mixture, drawing the mixture into the pipette; securing the hen; inserting the pipette into the hen's cloaca; and squeezing a bulb of the pipette to inject the mixture from the pipette into the cloaca.

In an embodiment, prior to applying the semen extender, the method also includes the steps of applying pressure to the front of the male bird's cloacal protuberance to open it slightly to expel fecal matter, and removing the fecal matter.

In an embodiment, prior to inserting the pipette into the hen's cloaca, the method further comprises the steps of applying pressure to the front of the hen's cloaca to open it slightly to expel fecal matter, and removing the fecal matter.

In an embodiment, the step of securing the male bird comprises the steps of holding the male bird belly up with a head of the male bird laid back against a wrist of a handler and a tail of the male bird pointing towards a front of a hand of the handler; holding the male bird's tail aside using one or more fingers of the handler; applying pressure to the front of the cloaca and holding one or more legs of the male bird out of the way using a thumb of the handler; and curling one or more fingers of the handler around a body of the male bird to restrain the male bird and keep one or more wings of the male bird in place.

In an embodiment, the step of securing the male bird further comprises the step of inserting the male bird into a holding device with the legs, the tail and a vent of the male bird protruding from the holding device.

In an embodiment, the step of securing the hen comprises the steps of holding the hen belly up with a head of the hen laid back against a wrist of a handler and a tail of the hen pointing towards a front of a hand of the handler; holding the hen's tail aside using one or more fingers of the handler; applying pressure to the front of the cloaca and holding one or more legs of the hen out of the way using a thumb of the handler; and curling one or more fingers of the handler around a body of the hen to restrain the hen and keep one or more wings of the hen in place.

In an embodiment, the step of securing the hen further comprises the step of inserting the hen into a holding device with the legs, the tail and a vent of the hen protruding from the holding device.

In an embodiment, the step of squeezing the cloacal protuberance includes repeatedly squeezing at a base of the cloacal protuberance and pushing upwards until semen appears at the tip of the cloacal protuberance.

In an embodiment, prior to securing the male bird, the method further comprises the step of isolating the male bird and the hen into separate cages to allow the male bird and the hen to pass feces.

In an embodiment, prior to applying a semen extender liquid to the tip of the male bird's cloacal protuberance, the method further comprises the step of trimming feathers surrounding the cloacal protuberance.

In an embodiment, prior to applying a semen extender liquid to the tip of the male bird's cloacal protuberance, the method further comprises the step of trimming guide feathers surrounding the tip of the cloacal protuberance.

In an embodiment, a first insemination is performed on the hen before a first egg is laid by the hen. In a preferred embodiment, the first insemination is performed on the hen two to five days before the first egg is laid by the hen. Following the laying of the first egg, an insemination is performed on the hen every morning until the hen stops laying eggs.

In an embodiment, a holding device for restraining a bird has a base, an arm extending upward from the base, and an open-ended receptacle connected to the upper end of the arm. The holding device is used to restrain an upper portion of the bird during procedures such as sperm collection and artificial insemination.

In an embodiment, the base has one or more stabilizers to secure the holding device to a workspace to prevent movement of the holding device during use.

In an embodiment, a length of the arm is adjustable.

In an embodiment, the arm is segmented, such that the shape of the arm can be manipulated.

In an embodiment, the receptacle is detachable from the arm.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION OF PREFERRED EMBODIMENTS

Figure 1:
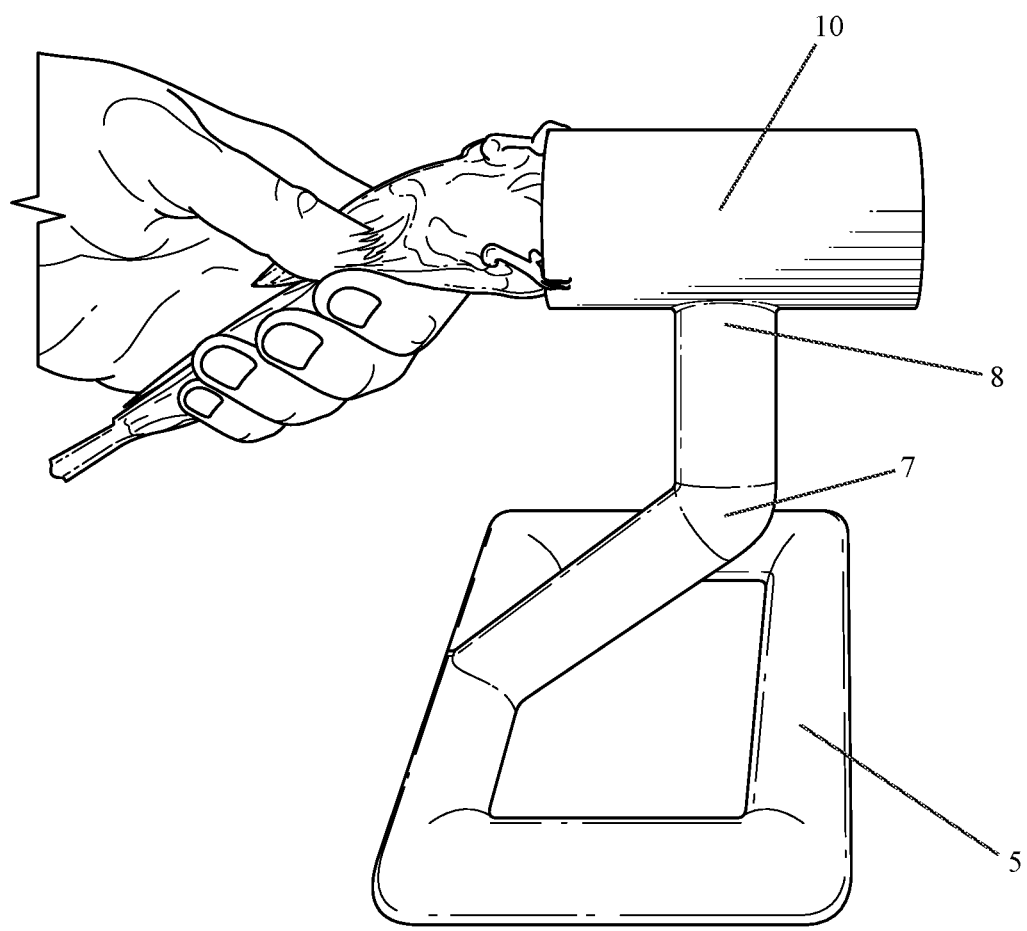
FIG. 1 is a perspective view of a holding device for restraining a bird, according to an embodiment of the present invention.
Figure 2:
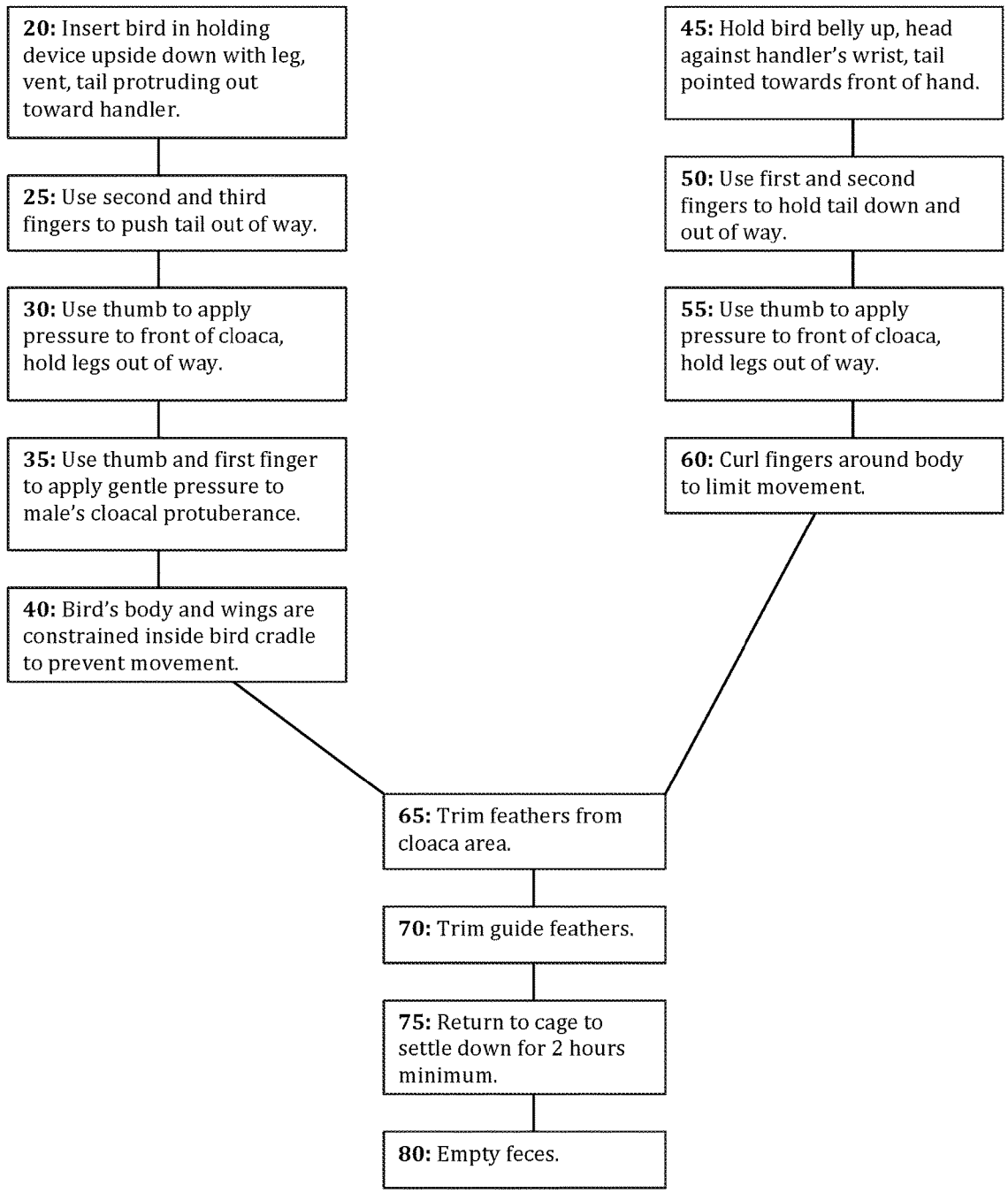
FIG. 2 is a flow chart of the preparation process for artificial insemination and sperm collection, with and without the holding device, according to an embodiment of the present invention.
Figure 3:
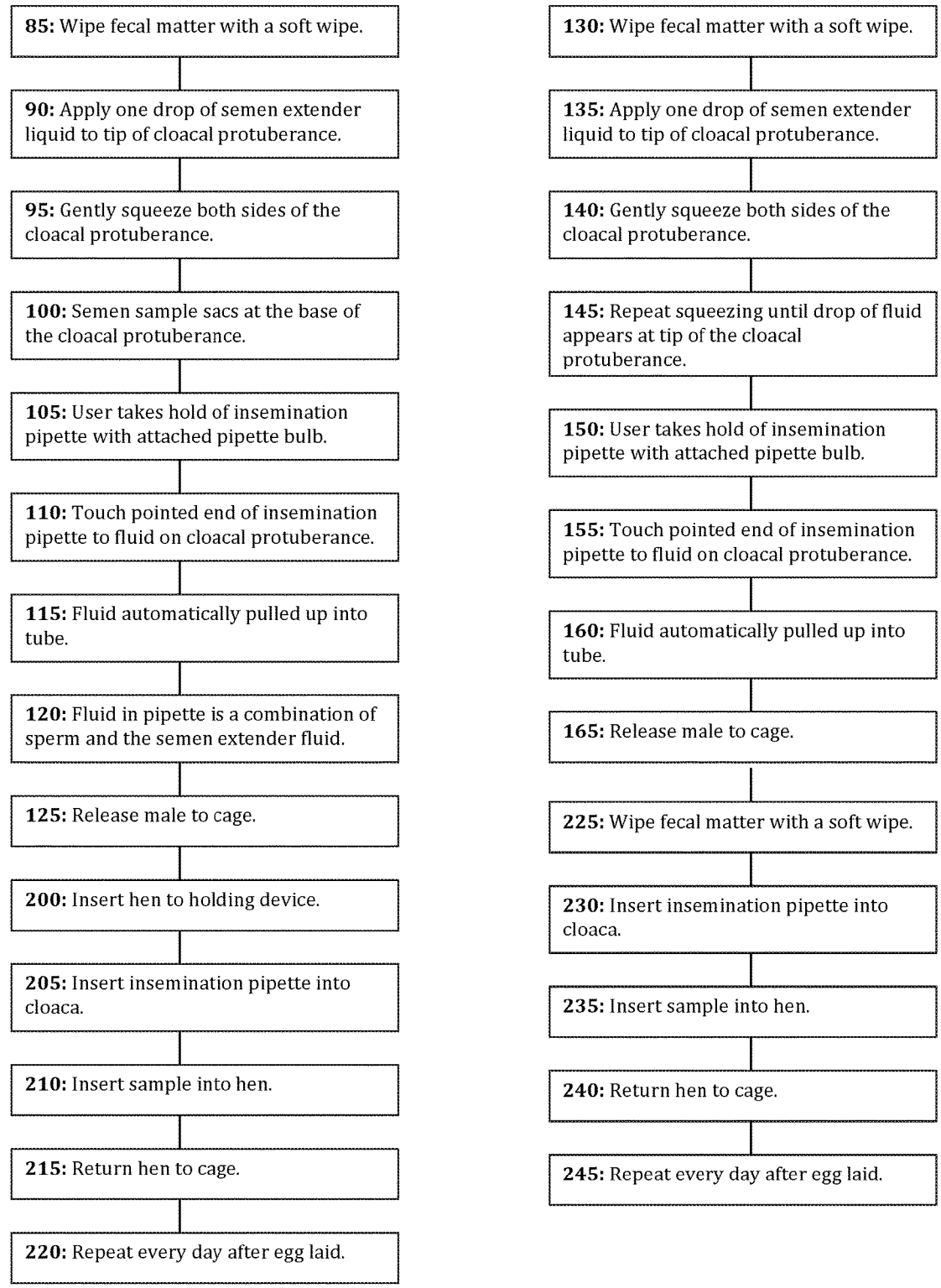
FIG. 3 is a flow chart of the artificial insemination and sperm collection processes, with and without the holding device, according to an embodiment of the present invention.

Preferred embodiments of the present invention and their advantages may be understood by referring to FIGS. 1-3, wherein like reference numerals refer to like elements.

With reference to FIG. 1, a holding, or restraint, device for restraining the male or the hen during the sperm collection or artificial insemination process, respectively, is shown. The holding device has a base 5, an arm 7 extending upward from the base 5, and an open-ended receptacle 10 connected to the upper end 8 of the arm 7. During the sperm collection and artificial insemination processes the male bird or the hen, respectively, is inserted head first into the receptacle 10 to restrain an upper portion, e.g., the head and the upper torso, of the bird while the handler holds and maintains control of the lower portion of the bird. In an embodiment, the receptacle 10 is a cylindrical pipe with an opening at one end, wherein the other end may be open or closed. In addition to sperm collection and artificial insemination, the holding device is useful for a number of other applications including, but not limited to, trimming a bird's nails or general restraint for conducting procedures requiring exposure to the bird's tail end.

In an embodiment, one or more stabilizers (not shown), such as a suction cup or a clamp, extend from the base. The stabilizer allows the holder to be secured to a workspace, such as a countertop, to prevent movement of the holder during use.

In an embodiment, the length of the arm 7 is adjustable, e.g., a telescoping arm. This is useful, for example, to accommodate handlers of varying heights. In a further embodiment, the arm 7 is jointed or segmented, allowing the shape of the arm to be manipulated. The arm 7 has one or more joints such that it has flexibility when motivated by the user, but holds its position when bent, in spite of the weight of the receptacle 10. In one embodiment, the arm 7 is continuously jointed to permit a variety of shaped configurations, such as a gooseneck that bends smoothly and holds the bent form. The joints are such that they rigidly maintain their position until altered or manipulated by the user. Again, this feature is useful in accommodating handlers of varying heights, and is also beneficial in accommodating various workspaces, since the arm can be bent or shaped around objects that would otherwise obstruct or inhibit its use.

In an embodiment, the receptacle 10 and the base 5 are detachable from the arm 7, for example, by use of a friction fit, snap fit, or threaded connection. However, one skilled in the art would understand and appreciate that other releasable connectors could be used to connect the receptacle 10 and the base 5 to the arm 7 without deviating from the scope of the present invention. This detachability of the receptacle 10 and the base 5 from the arm 7 allows a user to easily interchange receptacles and/or bases. This feature is useful, for example, when a handler is working with birds of various sizes, thus necessitating receptacles of various diameters and/or depths, or bases of various diameters and/or weights. This is also useful in the event maintenance on the receptacle 10 and/or the base 5 is required, for example, if the receptacle 10 and/or the base 5 breaks and needs to be replaced.

Preparation for Sperm Collection and Artificial Insemination

The male and the hen are restrained in the same manner for sperm collection or for insemination. With reference to FIG. 2, in step 20, the bird is inserted into the holding device upside down with its leg, vent and tail protruding out of one end toward the handler. In step 25, the handler's second and third fingers are used to push the tail down and out of the way. In step 30 the thumb of the opposite hand is used to apply very gentle pressure to the front of the cloaca, i.e., the cavity for excrement and reproduction, and hold the legs upwards and out of the way. In step 35, the thumb and first finger of the right hand is used to gentle apply upward pressure to the male's cloacal protuberance. In step 40 the bird's body and wings are constrained inside the bird cradle to prevent movement, while still leaving enough room for the bird's chest to move in and out, so that it can breathe easily during the process.

For individuals skilled in small bird handling and not wishing to use the holding device, the male and the hen are held in the hand in same manner for sperm collection or for insemination. In step 45 the bird is held belly up, i.e., on its back, with its head laid back against the handler's wrist and their tails pointing towards the front of the hand. In step 50, the handler's first and second fingers are used to hold the tail down and out of the way. In step 55 the thumb is used to apply very gentle pressure to the front of the cloaca, i.e., the cavity for excrement and reproduction, and hold the legs upwards and out of the way. In step 60 the remaining fingers curl gently around the bird's body to limit movement and keep the wings in place. This hold requires very little force and leaves the bird's chest free of restraint so that it can breathe easily during the process.

Before attempting to collect sperm, in step 65 the feathers are trimmed away from around the male's cloaca area. Optionally, in step 70 the guide feathers are trimmed away on the tip of the male bird's cloacal protuberance, i.e., the swelling of the male canary or finch's cloaca that occurs only during the breeding season, as these can quickly soak up any sperm samples before the breeder can collect them. After feather trimming, in step 75 the male should be returned to his cage and left alone to settle down for at least 2 hours before any attempts are made to collect semen.

The feathers should always be cut, and not pulled, as pulled feathers will grow back quickly and pulling feathers can cause unnecessary pain to the birds. The cutting of the feathers only needs to be done once at the beginning of each breeding season. Trim the feathers as short as possible, being extremely careful not to accidentally cut the cloacal protuberance.

In step 80, the male and the hen should be empty of any feces before attempting artificial insemination. Ideally, move both birds into separate cages with clean paper on the bottom, and leave them there until they pass feces. Keep the male and the hen in separate cages to prevent loss of the male's sperm on a possible unsuccessful mating with the hen.

Sperm Collection

In an embodiment, an artificial insemination kit is used to carry out the sperm collection and artificial insemination processes. The kit includes an artificial insemination manual, insemination pipettes, a rubber pipette bulb, semen extender, a dropper bottle, microscope slides, microscope cover slips, scissors, and wipes.

With reference to FIG. 3, once the male is inserted into the holding device, in step 85 gentle pressure is applied by the user with the thumb to the front of the bird's cloacal protuberance to open it slightly and remove any fecal matter with a soft wipe. Next, in step 90 the user applies one drop of the semen extender liquid to the tip of his cloacal protuberance. Then the user very gently squeezes on both sides of the cloacal protuberance with the free hand's thumb and first finger, in step 95. This gentle squeezing should begin at the base of the cloacal protuberance and push gently upwards. This is repeated a couple of times until a drop of fluid appears at the tip of the cloacal protuberance at step 100, which is the semen sample that has been gently squeezed out of the seminal sacs at the base of the cloacal protuberance. In step 105, the user takes hold of the insemination pipette with the attached pipette bulb. At step 110 the user gently touches the narrow, pointed end of the insemination pipette to the fluid on the cloacal protuberance. In step 115 the fluid will automatically be pulled up into the tube by capillary action—there is no need to use the red squeeze bulb to produce a vacuum at this time. In step 120 the fluid inside the pipette is now a combination of sperm and the semen extender fluid. In step 125 the male can now be released back into his cage.

For individuals skilled in small bird handling, and not wishing to use the holding device, use the restraint hold described above and in step 130 the user applies gentle pressure with your thumb to the front of the bird's cloacal protuberance to open it slightly and remove any fecal matter with a soft wipe. Next, in step 135 the user applies one drop of the semen extender liquid to the tip of his cloacal protuberance. Then in step 140 very gently the user squeezes on both sides of the cloacal protuberance with a free hand's thumb and first finger. This gentle squeezing should begin at the base of the cloacal protuberance and push gently upwards. In step 145 the user repeats the squeezing a couple of times until a drop of fluid appears at the tip of the cloacal protuberance, to produce the semen sample that has been gently squeezed out of the seminal sacs at the base of the cloacal protuberance. In step 150 the user takes hold of the insemination pipette with the attached pipette bulb. In step 155 the user very gently touches the narrow, pointed end of the insemination pipette to the fluid on the cloacal protuberance. In step 160 the fluid will automatically be pulled up into the tube by capillary action—there is no need to use the red squeeze bulb to create suction at this time. The fluid inside the pipette is now a combination of sperm and the semen extender fluid. In step 165 the male can now be released back into his cage.

The user must keep a hold of the pipette, being careful not to lose the sample by touching it to anything. The user immediately catches up the hen from the cage she was placed in, so long as she is empty of feces. It is important not to delay too long as the semen sample will dehydrate very quickly and all the sperm will die if this happens. Proceed with inseminating the hen as detailed below.

The complete sperm collection process should take no longer than 10-20 seconds. The process should be quick and very gentle to reduce stress and ensure there is never any damage to the male's delicate cloacal tissue. The user should be very careful not to rub the insemination pipette on the male's cloaca as this could cause bleeding and infection. It is recommended to just touch the end of the insemination pipette to the fluid only. The amount of semen collected will be very small, for example, only about 0.01 ml.

Canary and finch semen requires special handling to collect live, undamaged sperm. They release a dense mass of sperm that contains little fluid and is very prone to dehydration. It is important to add the semen extender to prevent instant drying in the insemination pipette. The semen extender also protects the sperm from being killed by fecal bacteria and provides a more pH balanced liquid environment for better mobility. This ensures the healthiest possible sample, with maximum numbers of live and undamaged sperm for fertilization.

Semen samples from individual birds can be very different in appearance. Some will be clear, while others are more white and thicker in consistency. Very large and watery samples often contain too much lymph fluid and are usually a result of excessive force being applied to the male's cloaca. Lymph fluid kills sperm, so be very gentle and quick when collecting samples from the male. Some samples will not contain sperm at all, so it is always best to examine the remainder of the sample under a microscope after inseminating the hen.

Males kept in a cage without a hen will produce larger and more frequent semen samples for insemination, since they are not losing semen through unsuccessful copulation attempts. Most males can be collected from once daily, but some will only give samples every two days.

Insemination Technique for the Female

The hen should be placed in a separate cage with clean paper prior to insemination. The female should be given enough time to defecate and empty her cloaca. If the hen releases a large amount of feces immediately following insemination, it is likely that the sperm sample will be expelled with the feces. Also, the bacteria in feces kills sperm and can prevent the eggs from being fertilized. The antibiotic in the semen extender protects and reduces the loss of sperm.

The ideal time for the first insemination should occur a couple of days before the first egg is laid. This is usually just before the hen finishes fully lining her nest. Further inseminations should be done after each egg is laid. Most canaries and finches lay their eggs at night or in the early morning. Insemination is best done in the morning just after the egg is laid for that day. This enables the sperm to fertilize the next yolk just as it is being released into the uterus. If the insemination is performed later in the day, it is more likely that the yolk is not in the stage where it can still be fertilized. To increase the probability of effective insemination, it is recommended to inseminate the hen a couple days before the first egg and then each morning until she has stopped laying. For very nervous hens, inseminate the first time and rely on the hen's ability to store sperm to fertilize the rest of the eggs. It is, however, not guaranteed that all the eggs will be fertilized by the one inseminated semen sample.

Insemination before the first egg is laid increases the ability of the hen to store sperm in her sperm storage tubules, as the semen sample is not getting pushed back out by the emerging egg. Older hens are less able to store semen for long periods of time and should be inseminated more frequently than younger hens.

The user must be very gentle when handling hens that are known to have developing eggs inside them. A user does not want to accidentally break an egg that is due to be laid, as this can seriously injure the hen. Also, removing eggs from the nest and storing them until the clutch is complete will prevent damage to the eggs during your efforts to catch the hen for insemination. The eggs can be replaced with plastic dummy eggs.

Insemination of hens must be performed carefully. The hen's cloaca is very delicate and easily prone to injury and infection. The insemination pipettes are rounded at their tip to prevent damage to the bird's cloaca. It should be inserted into the hen's cloaca no further than the line on the pipette delineating the limit of the extent to which it may be inserted. For canaries and finches, the distance indicated is typically no more than 5 mm (¼"). The position of the line so indicated may vary according to the species of bird for which a given embodiment of the kit is intended.

Method of Female Insemination

In step 200, insert the hen into the holding device and apply gentle pressure with the thumb to the front of the hen's cloaca to expel any fecal matter. Remove any feces with a soft wipe. Next, in step 205 gently insert the insemination pipette into the cloaca approximately 5 mm—this is less than ¼ inch for canaries and finches. In a preferred embodiment, the insemination pipette tip has rounded edges to prevent injury to the hen. In step 210, the user squeezes the rubber bulb on the large end of the insemination pipette until the sample is inseminated into the female. In step 215 the insemination pipette is removed and the hen is returned to her cage. In step 220 this is repeated every day in the early morning after each egg has been laid, until the clutch is complete and the hen is no longer laying.

For individuals skilled in small bird handling and not wishing to use the holding device, in step 225 they may use the restraint hold described above and apply gentle pressure with the thumb to the front of the hen's cloaca to expel any fecal matter. Remove any feces with a soft wipe. In step 230, the user gently insert the insemination pipette into the cloaca approximately 5 mm—this is less than ¼ inch for canaries and finches. In a preferred embodiment, the insemination pipette tip has rounded edges to prevent injury to the hen. In step 235 the user squeezes the rubber bulb on the large end of the insemination pipette until the sample is inseminated into the female. In step 240 the user removes the insemination pipette and returns the hen to her cage. In step 245 this is repeated every day in the early morning after each egg has been laid, until the clutch is complete and the hen is no longer laying.

Disease Control

Every sample of semen collected will be one of two different types. Those that are 'clean' and only contain sperm, and those that are 'contaminated' and also contain fecal matter as well as sperm. In a preferred embodiment, the semen extender contains an antibiotic that will ensure your hens stay healthy even when inseminated with slightly contaminated samples. The antibiotic also protects the sperm from fecal bacteria which can kill them.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

We claim:

1. A method of artificially inseminating a hen, comprising the steps of:
   a. securing a male bird;
   b. applying a semen extender liquid to a tip of a cloacal protuberance of the male bird;
   c. squeezing the cloacal protuberance to extract semen from the male bird into the semen extender liquid to form a mixture;
   d. applying a tip of a pipette to the mixture, drawing the mixture into the pipette;
   e. securing the hen;
   f. inserting the pipette into the hen's cloaca; and
   g. squeezing a bulb of the pipette to inject the mixture from the pipette into the cloaca.

2. The method of claim 1, wherein prior to applying the semen extender, the method further comprises the steps of:
   a. applying pressure to the front of the male bird's cloacal protuberance to open the cloacal protuberance to expel fecal matter; and
   b. removing the fecal matter.

3. The method of claim 1, wherein prior to inserting the pipette into the hen's cloaca, the method further comprises the steps of:
   a. applying pressure to the front of the hen's cloaca to open it slightly to expel fecal matter; and
   b. removing the fecal matter.

4. The method of claim 1, wherein the step of securing the male bird comprises the steps of:
   a. holding the male bird belly up with a head of the male bird laid back against a wrist of a handler and a tail of the male bird pointing towards a front of a hand of the handler;
   b. holding the male bird's tail aside using one or more fingers of the handler;
   c. applying pressure to the front of the cloaca and holding one or more legs of the male bird out of the way using a thumb of the handler; and
   d. curling one or more fingers of the handler around a body of the male bird to restrain the male bird and keep one or more wings of the male bird in place.

5. The method of claim 4, wherein the step of securing the male bird further comprises the step of inserting the male bird into a holding device with the legs, the tail and a vent of the male bird protruding from the holding device.

6. The method of claim 1, wherein the step of securing the hen comprises the steps of:
   a. holding the hen belly up with a head of the hen laid back against a wrist of a handler and a tail of the hen pointing towards a front of a hand of the handler;
   b. holding the hen's tail aside using one or more fingers of the handler;
   c. applying pressure to the front of the cloaca and holding one or more legs of the hen out of the way using a thumb of the handler; and
   d. curling one or more fingers of the handler around a body of the hen to restrain the hen and keep one or more wings of the hen in place.

7. The method of claim 6, wherein the step of securing the hen further comprises the step of inserting the hen into a holding device with the legs, the tail and a vent of the hen protruding from the holding device.

8. The method of claim 1, wherein the step of squeezing the cloacal protuberance comprises repeatedly squeezing at a base of the cloacal protuberance and pushing upwards until semen appears at the tip of the cloacal protuberance.

9. The method of claim 1, wherein prior to securing the male bird, the method further comprises the step of isolating the male bird and the hen into separate cages to allow the male bird and the hen to pass feces.

10. The method of claim 1, wherein prior to applying a semen extender liquid to the tip of the male bird's cloacal protuberance, the method further comprises the step of trimming feathers surrounding the cloacal protuberance.

11. The method of claim 1, wherein prior to applying a semen extender liquid to the tip of the male bird's cloacal protuberance, the method further comprises the step of trimming guide feathers surrounding the tip of the cloacal protuberance.

12. The method of claim 1, wherein a first insemination is performed on the hen two to five days before a first egg is laid by the hen, and wherein an insemination is performed on the hen every morning after the laying of the first egg until the hen stops laying eggs.

* * * * *